United States Patent [19]

Forfitt

[11] Patent Number: 5,705,930
[45] Date of Patent: Jan. 6, 1998

[54] GAS PATH ELECTROSTATIC SENSOR

[75] Inventor: Roy Forfitt, White Parish, England

[73] Assignee: Stewart Hughes Limited, Eastleigh, England

[21] Appl. No.: 446,605

[22] PCT Filed: Nov. 25, 1993

[86] PCT No.: PCT/GB93/02429

§ 371 Date: Sep. 20, 1995

§ 102(e) Date: Sep. 20, 1995

[87] PCT Pub. No.: WO94/12872

PCT Pub. Date: Jun. 9, 1994

[30] Foreign Application Priority Data

Nov. 30, 1992 [GB] United Kingdom ............... 9225057-0

[51] Int. Cl.⁶ .................................................. G01N 27/60
[52] U.S. Cl. ............................ 324/453; 324/452; 324/457; 324/553
[58] Field of Search ............................... 324/446, 449, 324/452, 453, 457, 553, 724; 340/627, 631; 73/61.42

[56] References Cited

U.S. PATENT DOCUMENTS

| 4,222,007 | 9/1980 | Comstock . | |
|---|---|---|---|
| 4,251,775 | 2/1981 | Michel . | |
| 4,433,298 | 2/1984 | Palm | 324/457 |
| 4,625,176 | 11/1986 | Champion et al. | 324/458 |
| 4,642,559 | 2/1987 | Slough . | |
| 4,760,342 | 7/1988 | Conrads et al. | 324/457 |
| 4,875,133 | 10/1989 | Kawamura | 324/457 X |
| 5,596,266 | 1/1997 | Mori et al. | 324/71.1 |

FOREIGN PATENT DOCUMENTS

| 137148 | 4/1985 | European Pat. Off. . |
| 1382226 | 1/1975 | United Kingdom . |
| 2012058 | 7/1979 | United Kingdom . |

*Primary Examiner*—Kenneth A. Wieder
*Assistant Examiner*—Glenn W. Brown
*Attorney, Agent, or Firm*—Hopgood, Calimafde Kalil & Judlowe

[57] ABSTRACT

A sensor installable within a gas turbine engine for sensing electrostatic charge therein. The sensor comprises a sensing plate and first and second shielding plates. The sensing plate has a first face with a first peripheral portion, and a second face with a second peripheral portion. The first and second shielding plates are spaced from and positioned relative to the first and second faces of the sensing plate, respectively, by a layer of electrically insulating material, so that electrostatic charge in the proximity of the sensor is sensed by both the first and second peripheral portions of the sensing plate.

6 Claims, 3 Drawing Sheets

FIG. 3
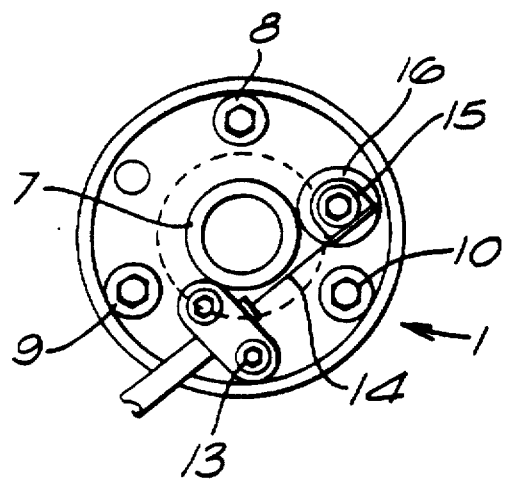
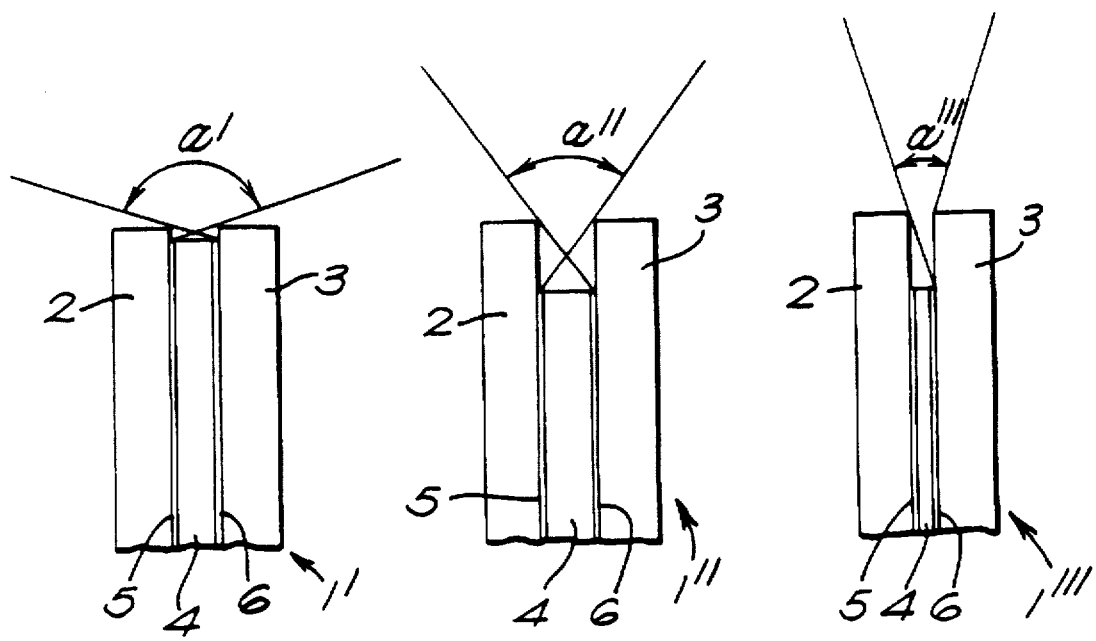
FIG. 5a   FIG. 5b   FIG. 5c

GAS PATH ELECTROSTATIC SENSOR

The invention relates to a sensor and particularly, but not exclusively, to a sensor for sensing electrostatic charge in the gas path of a gas turbine engine.

It has been known for some time that it is possible to detect the presence of electrostatic charge in the gas path of a gas turbine engine. Particles of debris naturally carry an electrostatic charge and by detecting such charge it is possible to monitor the passage of debris through an engine. Sensors can be placed at several positions along the gas path. For example, a sensor can be used at the air inlet to an engine in order to monitor debris ingested into the engine and another sensor can be used at the exhaust to monitor debris in the exhaust gases. Signals obtained from such sensors can be analysed for example by determining whether or not debris has been generated internally by, say, a blade rubbing against a fixed portion of the engine.

The environment of a gas turbine engine is hostile, particularly in parts of the engine after the combustion chamber where exhaust gases reach very high temperatures. Clearly, a sensor in this part of the engine must be capable of surviving in the hostile environment if it is to be of any use. One form of sensor that has hitherto been used comprises conductive material sprayed onto the inside of the engine body to form a loop sensor around the gas flow path. Such sensors are applied using plasma spraying techniques. Sprayed on sensors are difficult to connect to electrically and, using presently available materials, tend to fall off into the gas flow path thereby adding to the debris in the engine. Another loop sensor is disclosed in a European patent application published as EP-A-0 120 087. This sensor comprises a conductive loop placed behind the engine and is therefore only suitable for use in ground tests and is not suitable for use in continuously monitoring an engine when the engine is in use in say an aircraft. Loop sensors can detect the passage of charge at any point across the gas flow path but they also have a wide angle of view along the gas path. It is important to be able to see across the whole of the gas flow path in order that all debris therein can be detected but advantageously the view along the gas path should be narrow so that the sensor only sees a thin cross section of the path. A narrow field of view helps to reduce noise in signals produced by the sensor.

Another form of sensor that has hitherto been used comprises a probe mounted in an insulating body which can be fitted to a convenient location on the body of an engine. These sensors sense electrostatic charge passing a point, i.e. the point at which the sensor is mounted, in the gas path. The sensors generally have a wide conical field of view and often two or more sensors are required to achieve a field of view across the whole of the gas path. Thus, point sensors also suffer from the disadvantage that they have a wide field of view along the gas path. Point sensors can be designed to conform to the surface of the engine body thereby significantly reducing the unpredictable effects that could occur if the sensors were to intrude into the gas flow path. This enables point sensors to be retrofitted to existing engines without the need for extensive recalculation of gas flow behaviour to take account of any intrusion into the gas path. In practice point sensors, be they gas path intrusive or conformal, have a finite sensing area of a few square centimeters. For this reason conformal point sensors are also known as button sensors. Points sensors are thus not insubstantial in size. Therefore, retrofitting of point sensors requires the cutting of mounting holes in the body of the engine, thereby necessitating the recalculation of stresses within the engine to ensure that the engine will not be damaged by the retrofitting of the sensors. Clearly, this is undesirable but it is also very necessary because there are many designs of engine currently in service where debris sensing could be usefully employed for example in monitoring the health of the engine. Until the next generation of engine design comes along the recalculation of engine behavior will be required before sensors can be safely fitted to an engine. There are considerable savings in costs therefore in a sensor which minimizes engine body modifications and/or gas flow path intrusion.

According to the invention there is provided a sensor for sensing electrostatic charge, the sensor comprising a sensing plate having two faces and a peripheral face, and at least one shielding plate positioned relative to one face of the sensing plate so that in use sensing of electrostatic charge in the proximity of the sensor is by a portion of the peripheral face of the sensing plate.

The above and further features of the invention are set forth with particularity in the appended claims and together with advantages thereof will become clearer from consideration of the following detailed description of an exemplary embodiment of the invention given with reference to the accompanying drawings.

In the drawings:

FIG. 3 is a plan view of a first sensor;

FIG. 5 shows schematic views illustrating how the field of view of a sensor depends on the relative dimensions of various parts of the sensor.

Figure 1:
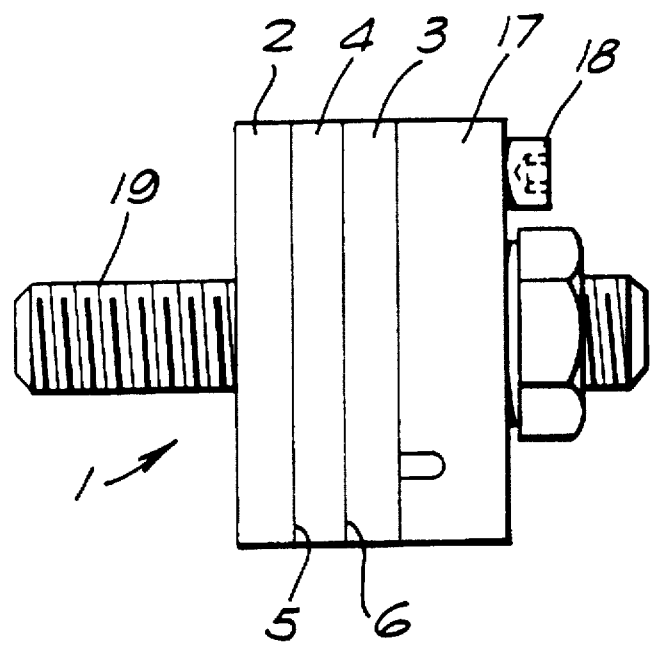
FIG. 1 is a schematic side elevation of a first sensor embodying the invention.
Figure 2:
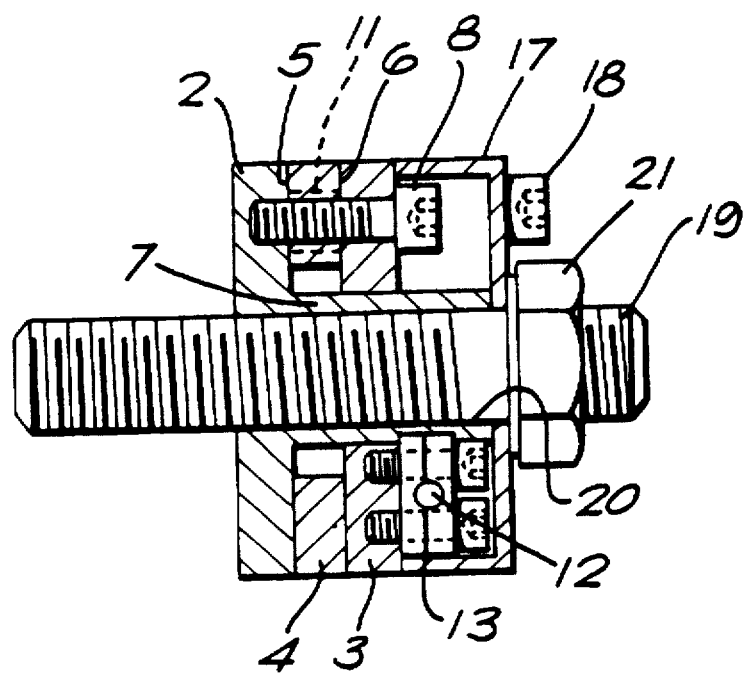
FIG. 2 is a sectional view of the first sensor.

Turning now to FIGS. 1 to 3 of the accompanying drawings, a sensor 1 comprises a front shield disc 2, a rear shield disc 3 and an annular sensing element 4 between the disc shields 2, 3 and separated therefrom by thin layers of insulation. As used herein the terms "front" and "rear" are merely to provide a frame of reference and otherwise have no particular significance. The front shield 2 is the portion of the sensor 1 which in use is nearest to the front of the engine and the rear shield 3 is the portion that will be nearest to the exhaust. The front and rear shields 2, 3 are made from a similar or the same material as that of the body of the engine in order to ensure that the sensor is sufficiently robust to survive in the hostile environment of the engine.

Likewise, the sensing element 4 is made from a conductive material similar or identical to that of the engine. The insulation layers 5, 6 may be made from mica or other suitable insulating material able to withstand the extreme temperatures and conditions within a gas turbine engine. In use the shields 2, 3 serve to shield the sensing element 4 from spurious electrostatic charges in the gas path of an engine in which the sensor is fitted upstream or downstream of the sensor.

As can best be seen from FIG. 2 the front shield comprises a supporting column 7 around which are placed the rear shield 3, the sensing element 4 and the insulating layers 5, 6. Securing bolts 8, 9 and 10 are provided to hold the various parts of the sensor together. The securing bolts 8 to 10 extend through respective holes 11 in the sensing element, the holes 11 being oversize in order to avoid electrical contact between the sensing element 4 and the bolts 8 to 10.

Signals from the sensor 1 are transmitted to signal conditioning and processing apparatus (not shown) via cable 12 which is secured to the rear shield by a clamp 13. The cable 12 comprises a conductor 14 which is connected to the sensing element 4 via a spacer 15 which extends through an oversize hole 16 in the rear shield 3 (see FIG. 3). Alternatively, the cable 12 may pass through the oversize hole 16 in the rear shield 3 with the conductor 14 being connected directly to the sensing element 4. A cover 17 of similar material to that of the front and rear shields 2, 3 is secured to the rear shield by a bolt 18 and provides protection for the cable connections thereunder.

Figure 4:
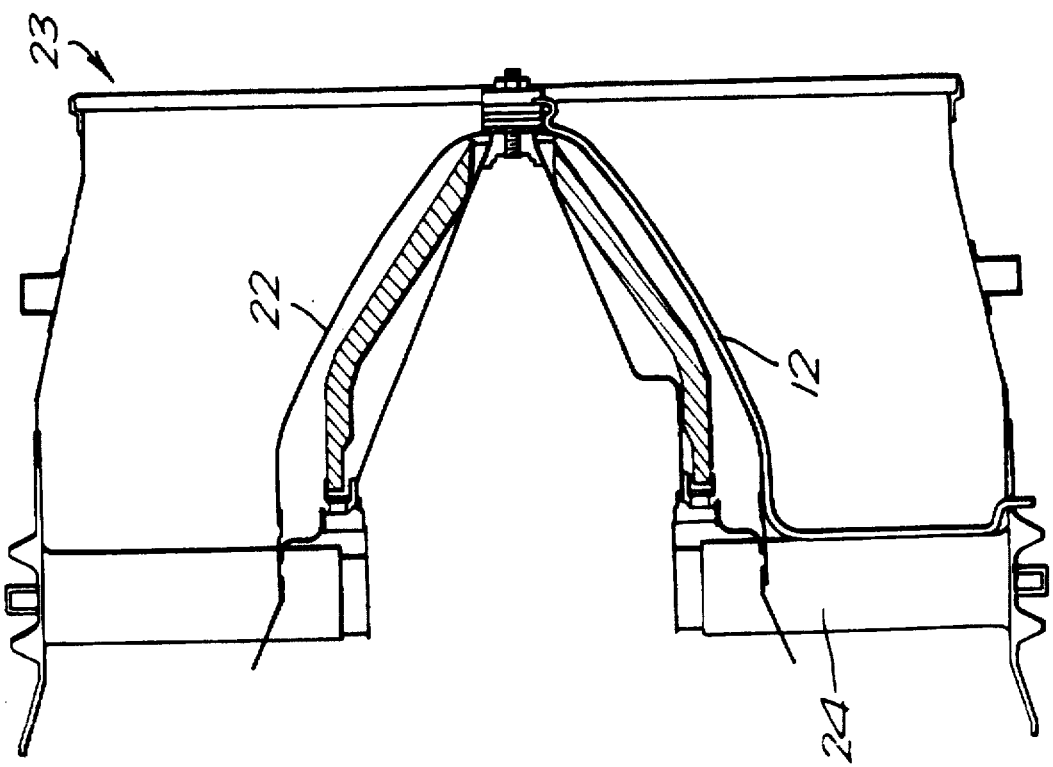
FIG. 4 is a schematic part-sectional view of the first sensor fitted to an engine.

In use a retaining stud 19 is passed through a bore 20 in the supporting column 7 and together with a retaining nut 21 is used to secure the sensor to a suitable location in an engine. FIG. 4 of the accompanying drawings shows the sensor 1 mounted to the rear or exhaust cone 22 of a gas turbine engine 23. As shown, the cable 12 is placed on the surface of the cone 22 and behind a stator 24 so as to exit from the body of the engine at a convenient location where it can be connected to signal conditioning and processing equipment (not shown). This form of fitting is not always desirable because the presence of the cable in the gas path affects the gas flow behavior. However, on most engines the exhaust cone 22 and its supporting stators 24 are hollow and the cable 12 can therefore be fed therethrough to a convenient position on the body of the engine and thus connection to the sensor 1 can be made without intrusion into the gas flow path of the engine.

The sensor 1 is thus designed to be placed centrally in the gas flow path of an engine and, because the sensing element 4 is circular, has the ability to sense electrostatic charge passing it at any position in the gas flow path. The field of view of the sensor along the gas flow path is determined by the relative dimensions of the front and rear shields 2, 3 and the sensing element 4. Turning now to FIG 5 of the accompanying drawings, there is shown (a) a portion of a sensor 1' having a wide field of view α', (b) a similar portion of a sensor 1" having a narrow field of view α", and (c) a similar portion of a sensor 1'" having an even narrower field of view α'". It should be clear from consideration of FIG. 5 that the field of view α of the sensor is determined both by the relative diameter of the sensing element and the shields and by the thickness of the sensing element. In FIG. 5(a) there is only a small different between the height of the sensing element 4 and the height of the shields 2, 3 and this results in a large angle of view α'. In FIG. 5(b) there is a large difference between the diameters and this results in a narrower angle of view α". The sensing element of FIG. 5(c) is of similar diameter to that of the sensing element in FIG. 5(b) but the thickness of the sensing element in FIG. 5(c) is significantly less thus causing the field of view α'" to be further narrowed.

Figure 6:
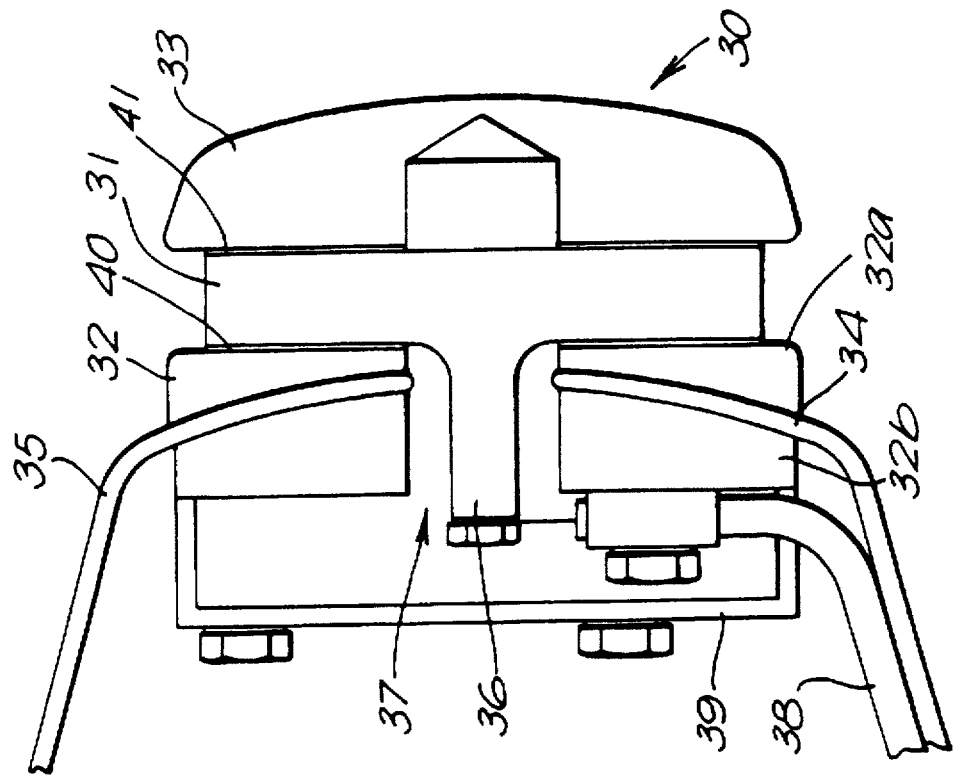
FIG. 6 is a schematic part-sectional view of a second sensor embodying the invention fitted to an engine.

In addition to altering the relative dimensions of parts of the sensor, the form of various parts of the sensor may be altered in order to make a sensor that is well suited to a specific engine. FIG. 6 of the accompanying drawings shows a sensor 30 designed for use in an engine such as a Rolls-Royce RB199 engine. The sensor 30 again comprises a sensing element 31 between front and rear shields 32, 33. The front shield 32 comprises two plates 32a, 32b which act as a clamp between which a wall portion 34 of an exhaust cone 35 is sandwiched thereby securing the sensor 30 to the cone 35. The sensing element 31 comprises a central pillar 36 which passes through an oversize hold 37 defined by the adaptor plates 32a, 32b to provide inside the cone 35 a connecting point for a cable 38. A cover 39 covers the front of the adaptor plate 32a. The rear shield 33 is designed to have a similar form to that of the exhaust cone 35. The front and rear shields 32, 33 are spaced from the sensing element 31 by insulating discs 40, 41.

An RB199 engine comprises an after burner (not shown) which is positioned in the gas path downstream of the exhaust cone 35. An engine with an after burner requires a sensor with a relatively narrow field of view in which electrostatic charge from the afterburner is not seen.

The sensing element therefore has a diameter which is significantly less than that of at least the rear shield 33. Of course, it is also desirable that the field of view of the sensor 30 does not include the combustion chamber (not shown) of the engine and therefore the diameter of the front shield 32 is significantly greater than that of the sensing element 31. The respective diameters of the front and rear shields need not be the same.

It will be appreciated by those possessed of the appropriate skills that the difference in diameter of the shields and the sensing element causes a step change in the surface of the sensor which could cause undesirable turbulence or other changes in the gas flow. The circumferential surface of the sensor should be designed with this in mind for example by blending-out any step change in the surface or incorporating any suitable aerodynamic design which minimizes the turbulence effect of the sensor.

Both of the above described sensors 1 and 30 provide all around vision in the gas path of a gas turbine engine through a narrow or otherwise predetermined field of view. Furthermore, both of the described sensors 1 and 30 are less sensitive to localised interference (noise) than the known loop and point or button sensors. This is because in the case of both the loop and the button sensors each incremental sensing area of the sensor is able to see electrostatic charge at each and every location within the whole field of view of the whole sensor. As a result the overall background noise sensed by the known sensors is relatively high. In contrast, in the sensors 1 and 30 each incremental sensing area can only see electrostatic charge in a small portion of the whole field of view. In any one direction there is a limited portion of the whole sensing area available for sensing and accordingly there is only a limited area for sensing localized interference. As a result, signals from the sensors 1 and 30 are less noisy than equivalent signals from previously known sensors. The sensors 1 and 30 can therefore be used to provide an engine monitoring system having an overall signal-to-noise ratio which is higher than has been possible hitherto.

Having thus described the present invention by reference to a preferred embodiment it is to be well understood that the embodiment in question is exemplary only and that modifications and variations such as will occur to those possessed of appropriate knowledge and skills may be made without departure from the spirit and scope of the invention as set forth in the appended claims and equivalents thereof.

I claim:

1. A sensor for sensing electrostatic charge, said sensor comprising:

a sensing plate having a first face with a first peripheral portion, and a second face with a second peripheral portion; and a first shielding plate positioned relative to said first face of said sensing plate so that electrostatic charge in the proximity of said sensor is sensed by said first peripheral portion of said sensing plate.

2. The sensor of claim 1, which further comprises a second shielding plate positioned relative to said second face of said sensing plate so that electrostatic charge in the proximity of the sensor is sensed by said second peripheral portion of said sensing plate, wherein said first and second shielding plates are spaced from said first and second faces of said sensing plate, respectively, by a layer of electrically insulating material.

3. The sensor of claim 2, wherein said first shielding plate extends beyond said first peripheral portion of said sensing plate, and said second shielding plate extends beyond said second peripheral portion of said sensing plate.

4. The sensor of claim 3, wherein said first shielding plate is secured relative to said sensing plate by at least one bolt extending through a first oversized hole formed in said first shielding plate, and said second shielding plate is secured relative to said sensing plate by at least one bolt extending through a second oversized hole formed in said second shielding plate.

5. The sensor of claim 1, wherein said second shielding plate comprises two or more plates for securing said sensor in position relative to a support surface.

6. The sensor of claim 1, installed within a gas turbine engine.

* * * * *